(12) United States Patent
Liu et al.

(10) Patent No.: US 10,946,121 B2
(45) Date of Patent: Mar. 16, 2021

(54) ABSORBABLE IRON-BASED ALLOY IMPLANTABLE MEDICAL DEVICE

(71) Applicant: Biotyx Medical (Shenzhen) Co., Ltd, Shenzhen (CN)

(72) Inventors: Ziqiang Liu, Shenzhen (CN); Haiping Qi, Shenzhen (CN); Wenjiao Lin, Shenzhen (CN); Deyuan Zhang, Shenzhen (CN)

(73) Assignee: Biotyx Medical (Shenzhen) Co., Ltd., Shenzhen (CN)

( * ) Notice: Subject to any disclaimer, the term of this patent is extended or adjusted under 35 U.S.C. 154(b) by 266 days.

(21) Appl. No.: 16/063,798

(22) PCT Filed: Jun. 27, 2016

(86) PCT No.: PCT/CN2016/087304
§ 371 (c)(1),
(2) Date: Jun. 19, 2018

(87) PCT Pub. No.: WO2017/117924
PCT Pub. Date: Jul. 13, 2017

(65) Prior Publication Data
US 2020/0215237 A1    Jul. 9, 2020

(30) Foreign Application Priority Data
Jan. 8, 2016 (CN) .......................... 201610016895.7

(51) Int. Cl.
*A61L 31/02* (2006.01)
*A61L 31/08* (2006.01)
*A61L 31/10* (2006.01)
*A61L 31/14* (2006.01)
*A61L 31/16* (2006.01)

(52) U.S. Cl.
CPC ........... *A61L 31/088* (2013.01); *A61L 31/022* (2013.01); *A61L 31/10* (2013.01); *A61L 31/148* (2013.01); *A61L 31/16* (2013.01); *A61L 2420/08* (2013.01)

(58) Field of Classification Search
CPC ........ A61F 2/00; A61F 2/0004; A61F 2/0013; A61F 2/0009; A61F 2/0018; A61F 2/063; A61F 2/06; A61F 2/30; A61L 31/00; A61L 31/022
See application file for complete search history.

(56) References Cited

U.S. PATENT DOCUMENTS

| 2010/0087914 A1 | 4/2010 | Bayer et al. |
| 2013/0261735 A1 | 10/2013 | Pacetti et al. |
| 2019/0022284 A1* | 1/2019 | Qi et al. ................. A61L 31/032 |

FOREIGN PATENT DOCUMENTS

| AU | 2015252144 A1 * | 11/2015 |
| AU | 2015252144 A1 * | 11/2015 |
| AU | 2015252144 A1 | 11/2015 |
| CN | 1796594 A | 7/2006 |
| CN | 101745147 A | 6/2010 |
| CN | 102228721 A | 11/2011 |
| CN | 102772831 A | 11/2012 |
| CN | 104587534 A | 5/2015 |
| CN | 104689369 A | 6/2015 |
| CN | 105030390 A | 11/2015 |

OTHER PUBLICATIONS

International Search Report dated Oct. 20, 2016 of corresponding International Application No. PCT/CN2016/087304; 6 pgs.
Chinese First Office Action dated Jan. 8, 2019, in connection with corresponding CN Application No. 201610016895.7 (13 pgs., including machine-generated English translation).

* cited by examiner

*Primary Examiner* — Micah Paul Young
(74) *Attorney, Agent, or Firm* — Maier & Maier, PLLC (57) ABSTRACT

An absorbable iron-based alloy implantable medical device, including an iron-based alloy substrate and a degradable polymer coating and a zinc-containing protector which are arranged on the surface of the iron-based alloy substrate. The zinc-containing protector is selected from zinc and/or a zinc alloy, or a mixture of zinc and/or a zinc alloy and a degradable binder. The weight percentage of the zinc and/or zinc alloy in the mixture is greater than or equal to 20% and less than 100%. The zinc-containing protector is capable of delaying the corrosion of the iron-based alloy substrate during the early stage of implantation, such that the iron-based alloy substrate essentially avoids corrosion during the early stage of implantation and the clinical mechanical property requirements for the device in the early stage of implantation can be satisfied.

15 Claims, 1 Drawing Sheet

ABSORBABLE IRON-BASED ALLOY IMPLANTABLE MEDICAL DEVICE

FIELD

The present application relates to the field of absorbable implanted medical devices, and more particularly relates to an absorbable iron-based alloy implanted medical device.

BACKGROUND

At present, the most frequently applied materials for an absorbable implanted medical device substrate include polymers, a magnesium-based alloy and an iron-based alloy, and the most frequently applied polymer is polylactic acid, which can be completely degraded and absorbed, with degradation products of carbon dioxide and water, but its mechanical properties are poor. The size of the polymer-based device should be larger than the metal-based device so that the polymer-based device has the same mechanical properties as the metal-based device, which limits application of the polymer-based device. The magnesium-based alloy and the iron-based alloy have advantages of convenience in processing and molding and high mechanical strength. However, as the magnesium-based alloy corrodes too quickly in a human body and may produce hydrogen during the corrosion, it is necessary to enlarge the size of a magnesium-based alloy device to accord with the mechanical property in the early stage of implantation, and in this way, the application of the magnesium-based alloy device is limited as well. In terms of clinical application, when the absorbable implanted medical device fulfills its expected use, after a diseased portion is cured and has recovered its normal shape and function (cured), so as to not cause a new biological compatibility problem, it is desirable for the device to completely corroded or degraded and absorbed by an organ as quickly as possible. According to different clinical application portions of the device, the recovery period is generally considered as 1 to 6 months, and within this period of time, the device is required to keep its structural integrality and have sufficient mechanical properties. The iron-based alloy has a good biological compatibility, but due to the slow corrosion of the iron-based alloy in the body, an iron-based alloy device would require a long time to be completely corroded after the diseased portion is cured; and, therefore, it is necessary to accelerate corrosion to shorten the corrosion cycle of the iron-based alloy device.

Research has shown that if the surface of the iron-based alloy is coated with a degradable polyester coating, its corrosion speed would be increased. Degradation of the degradable polyester coating in the body would lower the pH value of a local microenvironment near a device implantation position, thereby forming a local micro-acidic environment where the iron-based alloy is corroded faster to generate iron salt and/or iron oxides and/or iron hydroxides which are corrosion products.

For the iron-based alloy device of a predetermined specification, the corrosion speed of the iron-based alloy and whether the iron-based alloy is finally completely corroded or not are determined according to the amount of the degradable polyester coating and the type and the nature of degradable polyester. Under conditions that the type and the nature of the degradable polyester have been selected and the amount of the degradable polyester, which is sufficient to completely corrode an iron-based alloy substrate, have been determined, excessively high corrosion speed or local severe corrosion of the iron-based alloy would affect the structural integrality and the mechanical property of the iron-based alloy device in the early stage of implantation (1 to 6 months, namely the above-mentioned recovery period), therefore it is difficult for the device to meet the requirements for clinical application during the early stage of implantation. These defects are specifically as follows: (1) a degradation product of the degradable polyester coating layer is acidic, and there are small molecular residues with a higher degradation speed in the degradable polyester(for example, the standard monomer residue amount of the polylactic acid is less than 2%), that will result in faster corrosion of the iron-based substrate in the early stage of implantation, for example, after the device is implanted into a coronary artery for about 1 to 7 days, excessively fast corrosion and accumulation of the corrosion products cause incomplete endothelialization of the inner surface of the device, which increases the risk of acute thrombosis and subacute thrombosis; and (2) the heterogeneity of degradable polyester degradation easily leads to non-uniform corrosion of the iron-based alloy substrate, and local fast corrosion possibly results in breakage, so that the iron-based alloy substrate is unable to meet requirements of structural integrality and a requisite mechanical property during the early stage. Although the excessively fast corrosion of the iron-based alloy device during the early stage of implantation can be prevented by reducing the amount of the degradable polyester coating, the corrosion cycle of the iron-based alloy device would be prolonged. Therefore, for an iron-based alloy device that includes the degradable polyester, under the conditions that the type and the nature of the degradable polyester and the amount ratio of the degradable polyester to the iron-based alloy have been determined, it is necessary to seek a way to reduce the early corrosion speed of the iron-based substrate in the acidic environment formed by the degradable polyester to guarantee the mechanical property of the device during the early stage of implantation.

SUMMARY

An object of the present application is to provide an absorbable iron-based alloy implanted medical device. After being implanted into a body within 1 to 6 months, the absorbable iron-based alloy implanted medical device is corroded relatively slowly or is not totally corroded, and may meet the clinical requirement on a mechanical property of the device during the early stage of implantation within this period of time.

The absorbable iron-based alloy implanted medical device provided by the technical solution includes an iron-based alloy substrate, a degradable polymer disposed on the surface of the iron-based alloy substrate, and a zinc-containing protector disposed on the surface of the iron-based alloy substrate.

The zinc-containing protector may cover the entire surface of the iron-based alloy substrate, or may cover part of the surface of the iron-based alloy substrate. When the zinc-containing protector covers the entire surface of the iron-based alloy substrate, the degradable polymer covers at least part of the surface of the zinc-containing protector. When the zinc-containing protector does not cover the entire surface of the iron-based alloy substrate, non-covered regions and a corresponding non-covered region edge line of the iron-based alloy substrate may be exposed. The shortest distance between any point in the non-covered regions and the edge line on the surface of the iron-based alloy substrate is more than 0 mm and less than or equal to 40 mm; the area ratio of the zinc-containing protector is more than or equal to 15 percent, or further, the area ratio is more than or equal to 50 percent, or more further, the area ratio is more than or equal to 90 percent. Under a condition that any one area ratio of the zinc-containing protector in the above-mentioned 3 area ratios of the zinc-containing protector has been selected, the shortest distance is continuously shortened. For example, the shortest distance may be adjusted to be less than or equal to 5 mm, or further, the shortest distance may be adjusted to less than or equal to 1 mm, or further, the shortest distance may be adjusted to be less than or equal to 0.12 mm, or further, the shortest distance may be adjusted to be less than or equal to 0.05 mm. When the zinc-containing protector does not completely cover the surface of the iron-based alloy substrate, the degradable polymer may only cover at least part of the surface of the zinc-containing protector, or may cover different surface of the iron-based alloy substrate together with the zinc-containing protector in a staggered manner, or may cover at least part of the surface of the zinc-containing protector and cover at least part of the non-covered regions at the same time.

The zinc-containing protector is zinc and/or a zinc alloy, namely it is zinc, zinc alloy or a mixture of the zinc and the zinc alloy. The zinc-containing protector also may be a mixture of the zinc and/or the zinc alloy and a degradable adhesive, namely a mixture of the zinc and the degradable adhesive, or a mixture of the zinc alloy and the degradable adhesive, or a mixture of the zinc, the zinc alloy and the degradable adhesive. When the zinc-containing protector includes the degradable adhesive, the weight percentage of the zinc and/or zinc alloy is more than or equal to 20 percent and less than 100 percent.

The zinc-containing protector may be in electric contact with the iron-based alloy substrate, namely in direct contact with the surface of the iron-based alloy substrate, for example, the zinc-containing protector directly covers the surface of the iron-based alloy substrate in a way of a zinc-containing layer, or is embedded into the iron-based alloy substrate in a block or particle way. The zinc-containing protector also may be insulated from the iron-based alloy substrate; and at the moment, the device provided by the present application also may include an insulation layer disposed between the surface of the iron-based alloy substrate and the iron-based alloy substrate.

The iron-based alloy substrate may be pure iron or an iron-based alloy with a carbon content less than or equal to 2.11 weight percent, for example a product formed by nitriding and/or carburizing the pure iron.

The degradable polymer forms an acidic environment after being degraded, and an active drug may be mixed in the degradable polymer or no active drug is mixed in the degradable polymer. The active drug includes an anti-allergic drug. The anti-allergic drug is selected from the group consisting of an antihistamine type anti-allergic drug, an antileukotriens drug, a mast cell membrane stabilizer, a glucocorticoids anti-allergic drug or an immunoregulation anti-allergic drug. For example, the anti-allergic drug is selected from the group consisting of chlortrimeton, diphenhydramine, promethazine hydrochloride, cetirizine, clarityne, mizolastine, ebastine, astemizole, terfenadine, desloratadine, fexofenadine, cyproheptadine, ketotifen, levocetirizine, meclizine, efletirizine, carebastine, azelastine, decloxizine, chlorcyclizine, amlexanox, acrivastine, azatadine, mequitazine, levocabastine, setastine, sequifenadine, deptropine, pizotifen, pyrilamine, ranitidine, emedastine, epinastine, promethazine, montelukast, zafirlukast, tomelukast, zileuton, amlexanox, ibudilast, pemirolast, doxepin, verlukast, docebenone, sodium cromoglycate, sodium hydroxypropylcromate, nedocromil sodium, tranilast, tiaramide, repirinast, bufrolin, zaprinast, tazanolast, ozagrel, repirinast, dexamethasone, methylprednisolone, hydrocortisone, triamcinolone acetonide, corticosteroids, vitamin C, calcium, coenzyme Q10 or trypsin chymotrypsin.

Compared with the prior art, the absorbable iron-based alloy implanted medical device provided by the present application includes the zinc-containing protector. After the device is implanted into a body, the zinc-containing protector is corroded earlier than the iron-based alloy substrate, and generates a substance capable of preventing corrosion to avoid corrosion of the iron-based alloy substrate; only after the corrosion prevention substance generated by the corrosion of the zinc-containing protector is nearly completely cleared away by a tissue, the iron-based alloy substrate starts to be corroded fast, thereby ensuring that the iron-based alloy substrate meets the clinical requirement on the mechanical property during the early stage of implantation. In addition, the absorbable iron-based alloy implanted medical device of the present application has a smaller design size, and after being implanted, it produces a fewer of corrosion products and is shorter in complete absorption cycle.

BRIEF DESCRIPTION OF THE DRAWINGS

Further descriptions are made to the present disclosure in combination with accompanying drawings and embodiments as follows. In the drawings.

DETAILED DESCRIPTION

For the purpose of facilitating understanding of the present application, a more comprehensive description will be made below to the present application with reference to relevant accompanying drawings. In the drawings, preferred embodiments of the present application are provided. However, the present application may be implemented in many different ways, but is not limited to the embodiments described herein. On the contrary, the objective of providing these embodiments is to make disclosed contents of the present application more thorough and comprehensive.

Unless otherwise specified, all technical and scientific terms used in this text are the same as meanings of general understanding of technical persons skilled in the art of the present application. The terms used in the description are merely descriptive of the objectives of the specific embodiments, but not intended to limit the present application.

An absorbable implanted medical device of the present application includes an iron-based alloy substrate, a zinc-containing protector disposed on the surface of the substrate, and a degradable polymer coating disposed on the surface of the substrate. A main idea of the present application is that by additional arrangement of the zinc-containing protector on the surface of the iron-based alloy substrate, the zinc-containing protector is corroded firstly in an acidic environment formed by the degradable polymer layer and generates zinc phosphate having a corrosion prevention effect to controllably delay a time point when the iron-based alloy substrate starts to be corroded, thus achieving an effect that the iron-based alloy substrate is not corroded in the early stage (1 to 6 months) of implantation to ensure that the absorbable iron-based alloy implanted device has a structural integrality and a sufficient mechanical property in the early stage and the corrosion cycle of the iron-based alloy substrate is not prolonged.

As the zinc-containing protector may delay the time point when the iron-based alloy substrate starts to be corroded, the iron-based alloy substrate is not corroded basically within a protection period of the zinc-containing protector, and its mechanical properties do not change basically; therefore, the absorbable iron-based alloy implanted medical device of the present application only needs to ensure that its initial mechanical property before implantation may meet a clinical requirement on a lower limit during the early stage of implantation, and it is unnecessary for this absorbable iron-based alloy implanted medical device to have a relatively high mechanical property after the recovery period.

Therefore, compared with the prior art, the absorbable iron-based alloy implanted medical device of the present application has a decreased design size, which correspondingly decreases the amount of an iron-based alloy, thereby reducing corrosion products of the iron-based alloy.

Figure 1:
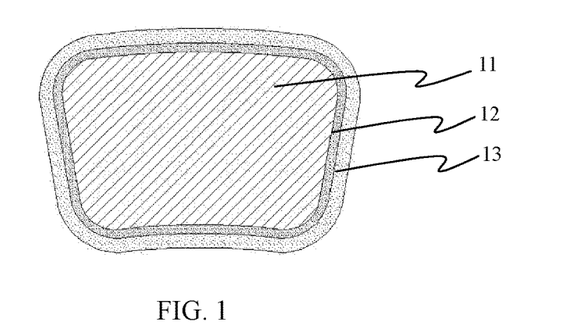
FIG. 1 is a sectional schematic diagram of an absorbable implanted medical device provided by one embodiment of the present application along its lengthwise direction, wherein a zinc-containing protector completely covers the entire surface of an iron-based alloy substrate.

With reference to FIG. 1, the absorbable iron-based alloy implanted medical device of the present application includes an iron-based alloy substrate 11, a zinc-containing protector 12 disposed on the iron-based alloy substrate 11, and a degradable polymer coating 13 disposed on the iron-based alloy substrate 11 and the zinc-containing protector 12. The zinc-containing protector 12 may be in electric contact with the iron-based alloy substrate 11, or also may be insulated from the iron-based alloy substrate 11, or may be directly disposed on the surface of the iron-based alloy substrate 11, or also may be separated from the iron-based alloy substrate 11 through a degradable insulation layer (not shown in the figure).

The iron-based alloy substrate 11 may be pure iron or an iron-based alloy with a carbon content less than or equal to 2.11 weight percent, for example a product obtained by carbonizing and/or nitriding the pure iron.

The material of the zinc-containing protector 12 may be pure zinc and/or a zinc alloy, or also may be a mixture of the zinc and/or the zinc alloy and a degradable adhesive. In the mixture of the zinc and/or the zinc alloy and the adhesive, the mass percentage of the zinc and/or the zinc alloy is more than or equal to 20 percent, but less than 100 percent. After the device is implanted into a body, the adhesive may be degraded or dissolved within short time to expose the zinc and/or the zinc alloy. The adhesive may be polyethylene glycol, polyvinyl alcohol, starch, cyclodextrin or water-soluble inorganic salt. The zinc-containing protector 12 may be prepared on the iron-based alloy substrate 11 via electroplating, spray deposition, vapor deposition (including vacuum plating, sputter coating, ion plating, molecular beam epitaxy coating and chemical vapor deposition), chemical coating, thermal coating, spray coating, dip coating, brush coating, electrostatic spinning, embedding and the like. It can be understood that an extra-degradable insulation layer such as a lecithin or starch layer can also be prepared on the surface of the iron-based alloy substrate 11 by adopting the above-mentioned methods, and then the zinc-containing protector 12 is prepared on the degradable insulation layer, so that the zinc-containing protector 12 can be insulated from the iron-based alloy substrate 11. It can be understood that the degradable insulation layer also may be a non-conductive material commonly used in an implant in this field.

Figure 2:
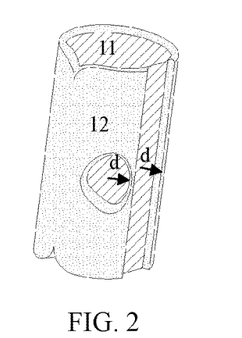
FIG. 2 is a schematic diagram of a degradable polymer-removed absorbable implanted medical device provided by another embodiment of the present application, wherein a zinc-containing protector covers part of the surface of an iron-based alloy substrate.
Figure 3:
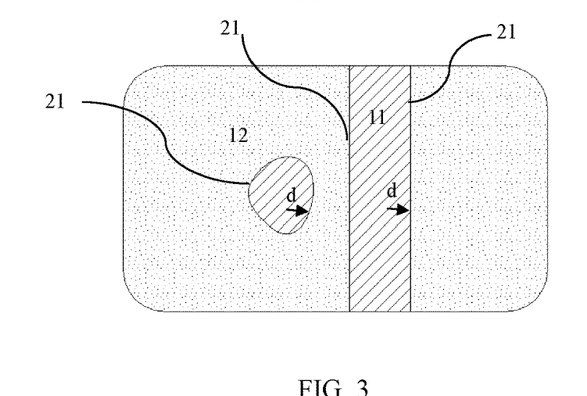
FIG. 3 is a schematic diagram of the outer surface, which is cut off and unfolded along an axial direction, of the degradable polymer-removed absorbable implanted medical device as shown in FIG. 2.
Figure 4:
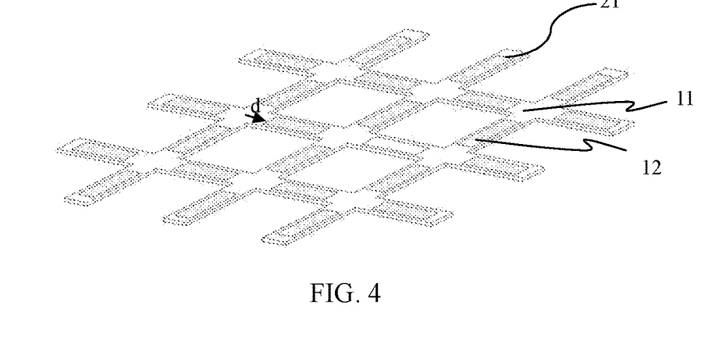
FIG. 4 is a schematic diagram of a degradable polymer-removed absorbable implanted medical device provided by another embodiment of the present application, wherein a zinc-containing protector runs through an iron-based alloy substrate along a thickness direction of the substrate.

There are many position relations between the zinc-containing protector 12 and the iron-based alloy substrate 11. As one implementation mode, as shown in FIG. 1, the zinc-containing protector 12 completely directly covers the surface of the iron-based alloy substrate 11, and the degradable polymer layer also directly completely covers the zinc-containing protector 12. As another implementation mode, as shown in the structural diagrams of degradable polymer-removed devices in FIG. 2 and FIG. 3, the zinc-containing protector 12 covers part of the surface of the iron-based alloy substrate 11, and part of the surface of the iron-based alloy substrate 11 is exposed. As another implementation mode, as shown in the structural diagram of a degradable polymer-removed device in FIG. 4, the zinc-containing protector 12 is embedded into the iron-based alloy substrate 11, and runs through the substrate along a thickness direction of the iron-based alloy substrate 11, and correspondingly, non-through portions of the iron-based alloy substrate 11 are called non-covered regions. It can be understood that the zinc-containing protector 12 also may be connected with the iron-based alloy substrate 11 in other ways, for example, the zinc-containing protector 12 is embedded into the iron-based alloy substrate 11 in a non-through manner, and its exposed end face may be flush with the surface of the iron-based alloy substrate 11, or may protrude from or be lower than the surfaces of the iron-based alloy substrate 11. When the zinc-containing protector does not completely cover the surface of the iron-based alloy substrate, namely no matter the zinc-containing protector covers part of the surface of the iron-based alloy substrate or is in contact with the iron-based alloy substrate in an embedding way or in other ways, it will define a covered region and a corresponding non-covered region edge line. With reference to FIGS. 2 to 4, the shortest distance between any point in the non-covered regions and the edge line 21 along the surface of the iron-based alloy substrate is defined as d which is more than 0 mm and less than or equal to 40 mm. The shortest distance is a length of the shortest line of connecting lines of any point in the non-covered regions and all points on the edge line 21. No matter the zinc-containing protector covers the entire surface of the iron-based alloy substrate or covers part of the surface of the iron-based alloy substrate or is embedded into the iron-based alloy substrate, its area ratio is more than or equal to 15 percent. A calculation method of the area ratio of the zinc-containing protector is as shown in Formula (1):

$$\text{Area ratio of the zinc-containing protector} = \frac{\text{the surface area of the exposed portion of the zinc-containing protector}}{\text{(the surface area of the exposed portion of the zinc-containing protector + the surface area of the exposed portion of the iron-based alloy substrate)}} \quad (1),$$

In this formula, the surface area of the exposed portion of the zinc-containing protector and the surface area of the exposed portion of the iron-based alloy substrate are both calculated on the basis of an iron-based alloy implanted device semi-finished product which includes the zinc-containing protector, but does not include the degradable polymer, namely a product obtained by removing the degradable polymer from the absorbable iron-based alloy implanted medical device as shown in FIGS. 2 to 4.

When the zinc-containing protector 12 completely covers the iron-based alloy substrate 11, namely the distribution of the zinc-containing protector 12 relative to the iron-based alloy substrate 11 accords with a condition that d is equal to 0, zinc elements in the zinc-containing protector 12 may generate zinc ions $Zn^{2+}$ after the zinc-containing protector 12 is in contact with the body fluid; $Zn^{2+}$ reacts with phosphate radicals $PO_4^{3-}$ in the body to generate insoluble zinc phosphate $Zn_3(PO_4)_2$, and the reaction equations are as shown in (2) and (3):

$$Zn = Zn^{2+} + 2e'' \qquad (2)$$

$$3\,Zn^{2+} + 2PO_4^{3-} \rightleftharpoons Zn_3(PO_4)_2 \qquad (3)$$

$Zn_3(PO_4)_2$ has a corrosion prevention effect, and its effect of delaying the corrosion of an iron-based alloy in the early stage of implantation of the device is mainly as follows: on one hand, the zinc phosphate is dissociated to generate phosphate ions, and condensed phosphate ions react with the surface of the iron-based alloy substrate 11 to form an adhering Fe—Zn—$P_2O_5$ compound film which covers the surface of the iron-based alloy substrate 11 to passivate the iron-based alloy substrate 11, thereby slowing down the corrosion of the iron-based alloy substrate 11; on the other hand, the zinc phosphate reacts with carboxyl generated by ionization of the degradable polymer to form a complex, and this complex may react with the iron corrosion products to form a compact protective film on the surface of the iron-based alloy substrate 11, thereby isolating the iron-based alloy substrate 11 from the environment in the body to restrain iron corrosion. With consumption of the zinc-containing protector 12, the amount of newly generated zinc ions $Zn^{2+}$ is reduced, and the balance of the reaction (3) moves leftwards, namely the zinc phosphate is gradually dissolved, and the iron-based alloy substrate 11 is gradually exposed; at the moment, the iron-based alloy substrate 11 starts to be corroded slowly; and when the zinc phosphate is used up, the iron-based alloy substrate 11 is completely exposed in an acidic environment formed by the degradation of the degradable polymer and starts to be corroded fast. It can be seen from the above that when the zinc-containing protector 12 completely covers the iron-based alloy substrate 11, its mechanism for delaying the corrosion of the iron-based alloy substrate 11 is not to protect the iron-based substrate by a sacrificial zinc anode, and this present application overcomes the preconception in the prior art.

When the zinc-containing protector 12 does not completely cover the surface of the iron-based alloy substrate 11, namely the distribution of the zinc-containing protector 12 relative to the iron-based alloy substrate 11 accords with a condition that d is more than 0, and when the zinc-containing protector 12 is in electric contact with the iron-based alloy substrate 11, the zinc-containing protector 12 protects the iron-based alloy substrate 11 in two aspects, namely protection from a sacrificial zinc anode due to formation of a galvanic couple pair by the zinc-containing protector 12 and the iron-based alloy substrate 11 and protection from the above-mentioned zinc phosphate which is a corrosion product. A zinc phosphate protection mechanism has the advantage of achieving an effective protection effect under a condition of an extremely small amount of zinc, but it needs a large amount of zinc for the protection from the sacrificial zinc anode due to the formation of the galvanic couple pair. Under the environment in the body, when the value d is gradually increased, the protection mechanism, which plays a leading role, of the zinc-containing protector 12 for the iron-based alloy substrate 11 is changed from the zinc phosphate protection mechanism into a sacrificial zinc anode protection mechanism.

In the present application, when the distribution of the zinc-containing protector 12 relative to the iron-based alloy substrate 11 accords with a condition that d is more than 0 mm and less than or equal to 40 mm, the zinc phosphate protection mechanism plays the leading role. In addition, when the absorbable iron-based alloy implanted medical device of the present application includes the degradable insulation layer disposed between the zinc-containing protector 12 and the iron-based alloy substrate 11, no galvanic couple pair will be formed between the zinc-containing protector 12 and the iron-based alloy substrate 11, namely when a condition letting the sacrificial zinc anode to protect the iron-based alloy substrate 11 may not be constituted, this device still may be hardly corroded in the early stage (1 to 6 months) of implantation, which indicates that the zinc-containing protector 12 can still protect the iron-based alloy substrate 11 by generating the zinc phosphate when insulated from the iron-based alloy substrate 11, and further indicates that in the absorbable iron-based implanted medical device of the present application, the mechanism of delaying the corrosion of the iron-based alloy substrate in the early stage of implantation is different from the mechanism of protecting the iron-based substrate by the sacrificial zinc anode, thereby overcoming the preconception in the prior art.

The amount (weight or volume) of the zinc-containing protector 12 is unrelated to the amount (weight or volume) of the iron-based alloy substrate 11, but is related to its own area ratio, the maximum value d and the type, the nature (such as a degree of crystallinity, a molecular weight and a polydispersity coefficient) and the thickness (or the mass) of the degradable polymer. The amount of the zinc-containing protector 12 may be variably selected according to the type and the specification of the device, a clinical performance requirement of the device, and an expected time length for maintaining a structural integrality and a sufficient mechanical property to adjust the time length that the zinc-containing protector 12 plays the protection role to be approximately matched with expected time for maintaining the structural integrality and the sufficient mechanical property of the iron-based alloy substrate 11.

The degradable polymer layer includes at least one degradable polymer, and acidic degradation products produced by its degradation, such as carboxylic acid. The degradable polymer may be selected from degradable polyester and/or degradable polyanhydride. The degradable polyester is any one of polylactic acid, polyglycolic acid, poly(lactic acid-glycolic acid), polycaprolactone, polyhydroxyalkanoate, polyacrylate, poly(ethylene succinate), poly(beta-hydroxybutyrate) and polyethylene glycol adipate, or is a physical blend of at least two of the polylactic acid, the polyglycolic acid, the poly(ethylene succinate), the poly(beta-hydroxybutyrate), the polycaprolactone, the polyethylene glycol adipate, a poly(lactic acid-glycolic acid) copolymer and a polyhydroxybutyrate-pentanoate copolymer, or is any one of copolymers formed by copolymerizing at least two of monomers forming the polylactic acid, the polyglycolic acid, the poly(ethylene succinate), the poly(beta-hydroxybutyrate), the polycaprolactone, the polyethylene glycol adipate, the poly(lactic acid-glycolic acid) copolymer and the polyhydroxybutyrate-pentanoate copolymer. The degradable polyanhydride is selected from at least one of poly1,3-bis(p-carboxyphenoxy)propane-sebacic acid, poly (erucic acid dimer-sebacic acid) or poly(fumaric acid-sebacic acid), or the degradable polymer is a copolymer formed by copolymerizing at least two of monomers forming the degradable polyester and the degradable polyanhydride.

The degradable polymer layer may further include an active drug, and may release therapeutic drugs during degradation. For example, for a vascular stent, this active drug may inhibit excessive intimal hyperplasia after the stent is implanted and reduce the occurrence rate of restenosis in a blood vessel. The active drug may be a drug for inhibiting vascular proliferation, such as taxol, sirolimus and its derivative, or an antiplatelet drug such as cilostazol, or an antithrombotic drug such as heparin, or an anti-inflammatory reaction drug such as dexamethasone, or an anti-allergic drug. The active drug also may be a mixture of the above-mentioned several drugs.

The degradable polymer layer may be prepared by adopting the following method: first dissolving the degradable polymer and the drug in an organic solvent (such as ethyl acetate, chloroform and the like) to form a mixed solution, then coating the entire surface or part of the surface of the iron-based alloy substrate 11 having the zinc-containing protector 12 with the mixed solution, and drying the surface to form a film. The processes used may be spray coating, dip coating, brush coating and electrostatic spinning, and the spray coating is preferred.

The absorbable iron-based alloy implanted medical device of the present application may be a vascular stent, an orthopedic implant, a gynecological implant, an andrology implant, a respiratory implant, or an orthopedic implant. A further detailed description will be made below to the present application in combination with specific embodiments by taking an iron-based alloy coronary stent as an example, but not intended to limit the scope of protection of the present application.

It should be noted that animal experiments in all the embodiments as follows show that under the action of the zinc-containing protector, the iron-based alloy stent may be hardly corroded during the early stage of implantation. The internal corrosion state of the iron-based alloy stent and whether a mechanical property requirement during the early stage is met or not are expressed by main measures of executing euthanasia to animals in which the stents are placed at different observation time points, such as 3 months, 6 months and 12 months, and then taking out each stent and tissue of a portion where the stent is placed and conducting a radial supporting strength and mass loss test on the stent and a blood vessel segment where the stent is placed.

The radial supporting strength test is carried out with a radial supporting strength tester produced by the MSI company: taking out the stent implanted into the body of the animal and the blood vessel segment, sucking out moisture to dry the surface, and then directly carrying out the test, thus obtaining the radial supporting strengths of the stent at different time points after the stent is implanted.

A way of testing the mass loss is as follows: implanting an iron-based alloy stent (with a degradable polymer) including an iron-based alloy substrate (which is a bare stent without the degradable polymer) with the mass of $M_0$ into an abdominal aorta of a rabbit, taking out the iron-based alloy stent implanted into the body of the animal and a tissue where the stent is placed at a preset observation time point, and then soaking the tissue and the stent in 1 mol/L sodium hydroxide solution to digest the tissue; removing zinc-containing protector residues from the surface of the iron-based alloy substrate, if any; then taking the iron-based alloy stent or a fragment thereof out of the solution, putting it into a solution at a certain concentration (such as a tartaric acid solution at the concentration of 3 percent, and/or an organic solution) for ultrasonic treatment to enable a corrosion product on its surface and the polymer layer to completely fall into or be dissolved in the solution, taking the residual non-corroded iron-based alloy stent or fragment thereof out of the solution, drying and weighing it, and recording the mass as $M_t$. A mass loss rate W is represented by a percentage of a difference value of the weight loss of a corroded and cleaned stent strut to the weight of the iron-based substrate, as shown in Formula 3:

$$W=(M_t-M_0)/M_0\times100\% \qquad (3)$$

W represents the mass loss rate $M_t$ represents the mass of the residual iron-based alloy stent substrate after corrosion $M_0$ represents the initial mass of the iron-based alloy stent substrate wherein when the mass loss rate W of the iron-based alloy substrate is less than 5 percent, it is defined that no corrosion occurs; and when the mass loss rate W of the iron-based alloy stent substrate is more than or equal to 90 percent, it is defined that full corrosion occurs.

Clinically, the diastolic pressure (low pressure) and the systolic pressure (high pressure) of a coronary vessel of a normal person are 60 to 120 mmHg, but the systolic pressure of a hypertension patient is up to 175 mmHg, namely 23.3 kPa. In the case of coronary artery spasm, the systolic pressure of the vessel is 400 mmHg, namely 55 kPa. A psychological stress state, a cold stimulation, a strenuous exercise, coronary atherosclerosis and a local stimulation to the coronary artery due to coronary angiogram as well as one-time heavy smoking or drinking may all induce coronary artery spasm. Thus, in order to provide an effective support for the coronary vessel, the stent should at least bear the systolic pressure of 23.3 kPa in case of pulsation of the coronary vessel, and should be equipped to bear the systolic pressure of 55 kPa in case of vasospasm. The design target of the iron-based alloy stent provided by each embodiment as follows is to meet the following clinical requirements: within preset time (for example, within 1 month, 2 months, 3 months or other time lengths shorter than 3 months) from the date of implantation, the iron-based alloy substrate is hardly corroded; and after being implanted, the iron-based alloy stent may provide effective support for 3 months; in the third month of implantation, the radial supporting strength is more than or equal to 55 kPa; and the corrosion cycle is longer than 6 months but shorter than or equal to 24 months.

The definition of the stent of the specification 30008 in each embodiment is as follows: after the stent is expanded under the action of a nominal expansion pressure of 8 atm, the nominal diameter is 3 mm, and the nominal length is 8 mm. The definition of the stent of the specification 30058 is as follows: after the stent is expanded under the action of a nominal expansion pressure of 8 atm, the nominal diameter is 3 mm, and the nominal length is 58 mm.

It should be noted that in each embodiment as follows, a normal fluctuation of the performance of a stent product within a designed allowable range, individual differences between the animals, an insufficient density of designed sampling points, and a system error unavoidably introduced by the test methods, may lead to fluctuations of monitored complete-no-corrosion time points, radial strength data and full-corrosion time points of the stent within a certain range in an actual test.

Embodiment 1

An absorbable iron-based alloy stent including a zinc-containing protector which can delay corrosion of the iron-based alloy substrate of the stent within 3 months after implantation. A preparation method is as follows: plating a zinc layer with a thickness of 800 nm on the surface of a nitrided iron stent of the specification 30008, which has an original radial supporting strength of 145 kPa and a mass of 4.5 to 5 mg, by adopting a vacuum evaporation method to completely cover the surface of the iron stent, and then spraying a poly-dl-lactic acid-ethyl acetate solution with a molecular weight of 200,000 to completely cover the surface of the zinc layer, and drying the surface to obtain the absorbable iron-based alloy stent with a poly-dl-lactic acid layer having a thickness of 12 μm. The stent is implanted into an abdominal aorta of a rabbit, and then is taken out after 3 months, and a mass loss test shows that the stent is not corroded, and its radial supporting strength is 145 kPa, and meets a 3-month mechanical property requirement of the early stage of implantation. The stent is taken out after 12 months, and the mass loss test shows that the stent is completely corroded.

Embodiment 2

An absorbable iron-based alloy stent including a zinc-containing protector that can delay corrosion of the iron-based alloy substrate of the stent within 1 month of implantation. A preparation method is as follows: galvanizing the surface of a nitrided iron stent of the specification 30008, which has an original radial supporting strength of 145 kPa and a mass of 4.5 to 5 mg, by adopting an electroplating method to obtain a zinc layer with an area ratio of 90 percent, d less than or equal to 0.02 mm, and a thickness of 600 nm, and then spraying a poly-dl-lactic acid-ethyl acetate solution with a molecular weight of 200,000 to completely cover the surface of the zinc layer and the exposed surface of the iron stent, and drying the surface to obtain the absorbable iron-based alloy stent with a poly-dl-lactic acid layer having a thickness of 10 μm. The stent is implanted into an abdominal aorta of a rabbit, and then is taken out after 1 month, and a mass loss test shows that the stent is not corroded. The stent is taken out after 3 months, and it is measured that the radial supporting strength of the stent is 80 kPa, and meets a 3-month mechanical property requirement of the early stage of implantation. The stent is taken out after 12 months, and the mass loss test shows that the stent is completely corroded.

Embodiment 3

An absorbable iron-based alloy stent including a zinc-containing protector that can delay corrosion of the iron-based alloy substrate of the stent within 2 months of implantation. A preparation method is as follows: galvanizing the surface of a nitrided iron stent of the specification 30008, which has an original radial supporting strength of 145 kPa and a mass of 4.5 to 5 mg, by adopting an electroplating method to obtain a zinc layer with an area ratio of 80 percent, d less than or equal to 0.05 mm and a thickness of 800 nm, and then spraying a poly-dl-lactic acid-ethyl acetate solution with a molecular weight of 200,000 to completely cover the surface of the zinc layer and the exposed surface of the iron stent, and drying the surface to obtain the absorbable iron-based alloy stent with a poly-dl-lactic acid layer having a thickness of 12 μm. The stent is implanted into an abdominal aorta of a rabbit, and then is taken out after 2 months, and a mass loss test shows that the stent is not corroded. The stent is taken out after 3 months, and it is measured that the radial supporting strength of the stent is 100 kPa, and meets a 3-month mechanical property requirement of the early stage of implantation. The stent is taken out after 10 months, and the mass loss test shows that the stent is completely corroded.

Embodiment 4

An absorbable iron-based alloy stent including a zinc-containing protector that can delay corrosion of an iron-based alloy substrate of the sent within 3 months of implantation. A preparation method is as follows: galvanizing the surface of a nitrided iron stent of the specification 30008, which has an original radial supporting strength of 145 kPa and a mass of 4.5 to 5 mg, by adopting a vacuum evaporation method to obtain a zinc layer which completely covers the surface of the iron stent and has a thickness of 800 nm, and then spraying a poly-dl-lactic acid-ethyl acetate (-sirolimus) solution with a molecular weight of 200,000 to completely cover the surface of the zinc layer, and drying the surface to obtain the absorbable iron-based alloy stent with a poly-dl-lactic acid (-sirolimus) layer having a thickness of 15 μm, where a mass ratio of poly-dl-lactic acid to sirolimus is 4:1. The stent is implanted into an abdominal aorta of a rabbit, and then is taken out after 3 months, and a mass loss test shows that the stent is not corroded, and it is measured that the radial supporting strength is 145 kPa, and meets a 3-month mechanical property requirement of the early stage of implantation. The stent is taken out after 13 months, and the mass loss test shows that the stent is completely corroded.

Embodiment 5

An absorbable iron-based alloy stent including a zinc-containing protector that can delay corrosion of the iron-based alloy substrate of the stent within 1 month of implantation. A preparation method is as follows: galvanizing the surface of a nitrided iron stent of the specification 30008, which has an original radial supporting strength of 145 kPa and a mass of 4.5 to 5 mg, by adopting an electroplating method to obtain a zinc layer which completely covers the outer surface of the iron stent, and has an area ratio of 25 percent, d less than or equal to 0.12 mm and a thickness of 6 μm, and then spraying a poly-dl-lactic acid solution with a molecular weight of 200,000 to completely cover the surface of the zinc layer and the exposed surface of the iron-based alloy stent, and drying the surface to obtain the absorbable iron-based alloy stent with a poly-dl-lactic acid layer having a thickness of 8 μm. The stent is implanted into an abdominal aorta of a rabbit, and then is taken out after 1 month, and a mass loss test shows that the stent is not corroded. The stent is taken out after 3 months, and it is measured that the radial supporting strength is 80 kPa, and meets a 3-month mechanical property requirement of the early stage of implantation. The stent is taken out after 12 months, and the mass loss test shows that the stent is completely corroded.

Embodiment 6

An absorbable iron-based alloy stent including a zinc-containing protector that can delay corrosion of the iron-based alloy substrate of the stent within 2 months of implantation. A preparation method is as follows: galvanizing the surface of a nitrided iron stent of the specification 30008, which has an original radial supporting strength of 145 kPa and a mass of 4.5 to 5 mg, by adopting a vacuum evaporation method to obtain a zinc layer with an area ratio of 60 percent, d less than or equal to 1 mm and a thickness of 2 μm; further disposing an insulation layer made of lecithin between the evaporated zinc layer and the surface of the nitrided iron stent to avoid electric contact between the zinc layer and the nitrided iron stent; and then spraying a poly-dl-lactic acid-ethyl acetate solution with a molecular weight of 200,000 to completely cover the surface of the zinc layer and the exposed surface of the iron stent, and drying the surface to obtain the absorbable iron-based alloy stent with a poly-dl-lactic acid layer having a thickness of 6 μm. The stent is implanted into an abdominal aorta of a rabbit, and then is taken out after 2 months, and a mass loss test shows that the stent is not corroded. The stent is taken out after 3 months, and it is measured that the radial supporting strength is 110 kPa, and meets a 3-month mechanical property requirement of the early stage of implantation. The stent is taken out after 24 months, and the mass loss test shows that the stent is completely corroded.

Embodiment 7

An absorbable iron-based alloy stent including a zinc-containing protector that can delay corrosion of the iron-based alloy substrate of stent within 1 month of implantation. A preparation method is as follows: slotting a nitrided iron stent strut of the specification 30008, which has an original radial supporting strength of 145 kPa and a mass of 4.5 to 5 mg, and embedding metal zinc in the slots, where the area ratio of all the embedded zinc is 35 percent, d is less than or equal to 5 mm, and the embedded zinc has a thickness of 20 μm; and then spraying a poly-dl-lactic acid-ethyl acetate solution with a molecular weight of 200,000 to completely cover the exposed surfaces of the embedded zinc and the exposed surface of the iron-based alloy stent, and drying the surface to obtain the absorbable iron-based alloy stent with a poly-dl-lactic acid layer having a thickness of 8 μm. The stent is implanted into an abdominal aorta of a rabbit, and then is taken out after 1 month, and a mass loss test shows that the stent is not corroded. The stent is taken out after 3 months, and it is measured that the radial supporting strength is 90 kPa. The stent is taken out after 18 months, and the mass loss test shows that the stent is completely corroded.

Embodiment 8

An absorbable iron-based alloy stent including a zinc-containing protector that can delay corrosion of an iron-based alloy substrate within 1 month of implantation. A preparation method is as follows: forming through holes in a nitrided iron stent strut of the specification 30058, which has an original radial supporting strength of 145 kPa and a mass of 26 to 30 mg, and embedding metal zinc in the through holes, where the area ratio of all the embedded zinc is 20 percent, and d is less than or equal to 40 mm; and then spraying a poly-dl-lactic acid-ethyl acetate solution with a molecular weight of 200,000 to completely cover the surface of a zinc layer and the exposed surface of the iron-based alloy stent, and drying the surface to obtain the absorbable iron-based alloy stent with a poly-dl-lactic acid layer having a thickness of 6 μm. The stent is implanted into an abdominal aorta of a rabbit, and then is taken out after 1 month, and a mass loss test shows that the stent is not corroded. The stent is taken out after 3 months, and it is measured that the radial supporting strength is 90 kPa. The stent is taken out after 18 months, and the mass loss test shows that the stent is completely corroded.

Embodiment 9

An absorbable iron-based alloy stent including a zinc-containing protector that can delay corrosion of the iron-based alloy substrate of the stent within 2 months of implantation. A preparation method is as follows: selecting a nitrided iron stent of the specification 30008, which has an original radial supporting strength of 145 kPa and a mass of 4.5 to 5 mg, ultrasonically dispersing nano zinc powder and polyethylene glycol (with a weight-average molecular weight of 6,000) in an ethyl alcohol solution to obtain a suspension solution, where a mass ratio of the zinc powder to the polyethylene glycol is 1:1; then coating the whole surface of the iron stent with the suspension solution via spray coating, and drying the surface to obtain an absorbable iron-based alloy stent with a zinc-polyethylene glycol layer having a thickness of 2 μm; and spraying a poly-dl-lactic acid-ethyl acetate solution with a molecular weight of 200,000 to completely cover the surface of the zinc-polyethylene glycol layer, and drying the surface to obtain the absorbable iron-based alloy stent with a poly-dl-lactic acid layer having a thickness of 12 μm. The stent is implanted into an abdominal aorta of a rabbit, and then is taken out after 2 months, and a mass loss test shows that the stent is not corroded. The stent is taken out after 3 months, and it is measured that the radial supporting strength is 100 kPa, and meets a 3-month mechanical property requirement of the early stage of implantation. The stent is taken out after 10 months, and the mass loss test shows that the stent is completely corroded.

Embodiment 10

An absorbable iron-based alloy stent including a zinc-containing protector that can delay corrosion of the iron-based alloy substrate of the stent within 1 month of implantation. A preparation method is as follows: galvanizing the surface of a nitrided iron stent of the specification 30008, which has an original radial supporting strength of 145 kPa and a mass of 4.5 to 5 mg, by adopting an electroplating method to obtain a zinc layer which covers the inner surface and part of the side surface of the iron stent, where the zinc layer has an area ratio of 50 percent, d less than or equal to 0.08 mm and a thickness of 4 μm; and then spraying a poly-dl-lactic acid-ethyl acetate solution with a molecular weight of 200,000 to completely cover the exposed surface of the iron-based stent, and drying the surface to obtain the absorbable iron-based alloy stent with a poly-dl-lactic acid layer having a thickness of 15 μm. The stent is implanted into an abdominal aorta of a rabbit, and then is taken out after 1 month, and a mass loss test shows that the stent is not corroded. The stent is taken out after 3 months, and it is measured that the radial supporting strength is 80 kPa, and meets a 3-month mechanical property requirement of the early stage of implantation. The stent is taken out after 18 months, and the mass loss test shows that the stent is completely corroded.

Contrast 1

This contrast provides a nitrided iron bare stent (namely a stent not including a degradable polymer and a zinc-containing protector) of the specification 30008, and it has an original radial strength of 145 kPa and a mass of 4.5 to 5 mg. The stent is implanted into an abdominal aorta of a rabbit. After 3 months, the stent is taken out, and a mass loss test shows that the stent is not corroded, and it is measured that the radial supporting strength of the stent is 140 kPa and meets a 3-month mechanical property requirement of the early stage of implantation. The stent is taken out after 24 months of the implantation, a mass loss test shows that the stent is not completely corroded, which indicates that the nitrided iron stent without the degradable polymer layer has corroded too slowly, and the corrosion cycle is too long.

Contrast 2

This contrast provides an absorbable iron-based stent, and its preparation method is as follows: coating the surface of a nitrided iron stent of the specification 30008, which has an original radial strength of 145 kPa and a mass of 4.5 to 5 mg, with a poly-dl-lactic acid-ethyl acetate solution with a molecular weight of 200,000 via spray coating to completely cover the whole surface of the stent, and drying the surface to obtain the absorbable iron-based alloy stent with a poly-dl-lactic acid coating layer having a thickness of 12 μm. The stent is implanted into an abdominal aorta of a rabbit, and then is taken out after 2 months, and it is found that struts of the stent are corroded extremely badly, and multiple positions are broken. The stent is taken out after 3 months, and it is measured that the radial supporting strength of the stent is less than 55 kPa, and a mass loss test shows that the stent is completely corroded, which indicates that the stent has corroded too fast and may not meet the mechanical property requirement in the early stage.

Contrast 3

This contrast provides an absorbable iron-based stent, and its preparation method is as follows: coating the surface of a nitrided iron stent of the specification 30008, which has an original radial strength of 175 kPa and a mass of 5.5 to 6 mg, with a poly-dl-lactic acid-ethyl acetate solution with a molecular weight of 200,000 via spray coating to completely cover the entire surface of the stent, and drying the surface to obtain the absorbable iron-based alloy stent with a poly-dl-lactic acid-ethyl acetate coating layer having a thickness of 10 μm. The stent is implanted into an abdominal aorta of a rabbit, and then is taken out after 1 month, and it is found that struts of the stent are corroded to a certain extent. The stent is taken out after 3 months, and it is measured that the radial supporting strength of the stent is 80 kPa and meets a 3-month mechanical property requirement in the early stage of implantation. The stent is taken out after 12 months of the implantation, and a mass loss test shows that the stent is completely corroded.

It can be seen from all the above embodiments, in the absorbable iron-based alloy stent of each embodiment, by the disposing the zinc-containing protector, the iron substrate is hardly corroded within the period that the zinc-containing protector plays the protection effect, and may meet the 3-month mechanical property requirement in the early stage of the implantation. By adjustment of the amounts of the zinc-containing protectors in all the embodiments, the time lengths, which correspond to the amounts of the zinc-containing protectors, that the zinc-containing protectors are consumed in the body are approximately matched with expected time lengths that the iron-based alloy is not corroded, thus realizing adjustment of the time lengths that the stent is not corroded in the early stage of implantation. By comparison with Contrast 1, the corrosion cycles of the stents provided by Embodiments 1 to 10 are shorter. By comparison with Contrast 2, the stent provided by Embodiment 3 is not corroded within 2 months of the early stage of implantation, and keeps a structural integrity and a sufficient mechanical support in the third month of implantation. By comparison with Contrast 3, the stent provided by Embodiment 2 adopts a smaller amount of the iron substrate on the premise of guaranteeing the same corrosion cycle and a sufficient mechanical support in the third month, so that it can be expected that the amount of corrosion products which is produced in the subsequent process would be less and the full absorption cycle is shorter.

The above embodiments only express several implementation modes of the present application, and their descriptions are relatively specific and detailed, but not intended to limit the scope of the present application thereby. It should be noted that an ordinary person skilled in the art can make various deformations and improvements without departing from the concept of the present application, and these deformations and improvements shall all fall within the scope of protection of the present application. Thus, attached claims for the scope of protection of the present application shall prevail.

The invention claimed is:

1. An absorbable iron-based alloy implanted medical device, comprising:
    an iron-based alloy substrate and a degradable polymer disposed on the surface of the iron-based alloy substrate, further comprising a zinc-containing protector disposed on the surface of the iron-based alloy substrate,
    wherein the zinc-containing protector is zinc and/or a zinc alloy, or a mixture of the zinc and/or the zinc alloy and a degradable adhesive;
    in the mixture, the weight percentage of the zinc and/or zinc alloy is more than or equal to 20 percent and less than 100 percent, and
    the zinc-containing protector covers at least part of the iron-based alloy substrate such that there are either no non-covered regions or non-covered regions with corresponding non-covered region edge lines in which a shortest distance between the non-covered regions and the edge line on the surface of the iron-based alloy substrate is less than or equal to 40 mm.

2. The absorbable iron-based alloy implanted medical device according to claim 1, wherein the zinc-containing protector covers every part of the surface of the iron-based alloy substrate so there are no non-covered regions, and the degradable polymer covers at least part of the surface of the zinc-containing protector.

3. The absorbable iron-based alloy implanted medical device according to claim 1, wherein the zinc-containing protector covers part of the surface of the iron-based alloy substrate, and the non-covered regions and the corresponding non-covered region edge line are exposed;
    the shortest distance between any point in the non-covered regions and the edge line on the surface of the iron-based alloy substrate is less than or equal to 40 mm; and
    an area ratio of the zinc-containing protector is more than or equal to 15 percent.

4. The absorbable iron-based alloy implanted medical device according to claim 3, wherein the shortest distance is less than or equal to 5 mm.

5. The absorbable iron-based alloy implanted medical device according to claim 3, wherein the degradable polymer covers at least part of the surface of the zinc-containing protector, or the zinc-containing protector and the degradable polymer cover different surfaces of the iron-based alloy substrate together in a staggered manner, or the degradable polymer covers at least part of the surface of the zinc-containing protector and also covers at least part of the non-covered regions at the same time.

6. The absorbable iron-based alloy implanted medical device according to claim 1, wherein the medical device further comprises an insulation layer disposed on the surface of the iron-based alloy substrate, and the insulation layer separates the iron-based alloy substrate from the zinc-containing protector.

7. The absorbable iron-based alloy implanted medical device according to claim 1, wherein the zinc-containing protector is in direct contact with the surface of the iron-based alloy substrate.

8. The absorbable iron-based alloy implanted medical device according to claim 7, wherein the zinc-containing protector is embedded into the iron-based alloy substrate.

9. The absorbable iron-based alloy implanted medical device according to claim 1, wherein the iron-based alloy substrate is pure iron or an iron-based alloy with a carbon content less than or equal to 2.11 weight percent.

10. The absorbable iron-based alloy implanted medical device according to claim 1, wherein an active drug is mixed in the degradable polymer.

11. The absorbable iron-based alloy implanted medical device according to claim 10, wherein the active drug comprises an anti-allergic drug; and
the anti-allergic drug is selected from the group consisting of an antihistamine type anti-allergic drug, an antileukotriens drug, a mast cell membrane stabilizer, a glucocorticoids anti-allergic drug or an immunoregulation anti-allergic drug.

12. The absorbable iron-based alloy implanted medical device according to claim 11, wherein the anti-allergic drug is selected from the group consisting of chlortrimeton, diphenhydramine, promethazine hydrochloride, cetirizine, clarityne, mizolastine, ebastine, astemizole, terfenadine, desloratadine, fexofenadine, cyproheptadine, ketotifen, levocetirizine, meclizine, efletirizine, carebastine, azelastine, decloxizine, chlorcyclizine, amlexanox, acrivastine, azatadine, mequitazine, levocabastine, setastine, sequifenadine, deptropine, pizotifen, pyrilamine, ranitidine, emedastine, epinastine, promethazine, montelukast, zafirlukast, tomelukast, zileuton, amlexanox, ibudilast, pemirolast, doxepin, verlukast, docebenone, sodium cromoglycate, sodium hydroxypropylcromate, nedocromil sodium, tranilast, tiaramide, repirinast, bufrolin, zaprinast, tazanolast, ozagrel, repirinast, dexamethasone, methylprednisolone, hydrocortisone, triamcinolone acetonide, corticosteroids, vitamin C, calcium, coenzyme Q10 or trypsin chymotrypsin.

13. The absorbable iron-based alloy implanted medical device according to claim 1, wherein the degradable polymer is degradable polyester and/or degradable polyanhydride; the degradable polyester is any one of polylactic acid, polyglycolic acid, poly(lactic acid-glycolic acid), polycaprolactone, polyhydroxyalkanoate, polyacrylate, poly(ethylene succinate), poly(beta-hydroxybutyrate) and polyethylene glycol adipate, or is a physical blend of at least two of the polylactic acid, the polyglycolic acid, the poly(ethylene succinate), the poly(beta-hydroxybutyrate), the polycaprolactone, the polyethylene glycol adipate, a poly(lactic acid-glycolic acid) copolymer and a polyhydroxybutyrate-pentanoate copolymer, or is any one of copolymers formed by copolymerizing at least two of monomers forming the polylactic acid, the polyglycolic acid, the poly(ethylene succinate), the poly(beta-hydroxybutyrate), the polycaprolactone, the polyethylene glycol adipate, the poly(lactic acid-glycolic acid) copolymer and the polyhydroxybutyrate-pentanoate copolymer, The degradable polyanhydride is selected from at least one of poly1,3-bis(p-carboxyphenoxy)propane-sebacic acid, poly(erucic acid dimer-sebacic acid) or poly(fumaric acid-sebacic acid), or the degradable polymer is a copolymer formed by copolymerizing at least two of monomers forming the degradable polyester and the degradable polyanhydride.

14. The absorbable iron-based alloy implanted medical device according to claim 1, wherein the zinc-containing protector covers part of the surface of the iron-based alloy substrate, and the non-covered regions and the corresponding non-covered region edge line are exposed;
the shortest distance between any point in the non-covered regions and the edge line on the surface of the iron-based alloy substrate is less than or equal to 40 mm; and
an area ratio of the zinc-containing protector is more than or equal to 50 percent.

15. The absorbable iron-based alloy implanted medical device according to claim 1, wherein the zinc-containing protector covers part of the surface of the iron-based alloy substrate, and the non-covered regions and the corresponding non-covered region edge line are exposed;
the shortest distance between any point in the non-covered regions and the edge line on the surface of the iron-based alloy substrate is less than or equal to 40 mm; and
an area ratio of the zinc-containing protector is more than or equal to 90 percent.

* * * * *